(12) United States Patent
Piper

(10) Patent No.: US 9,953,820 B2
(45) Date of Patent: Apr. 24, 2018

(54) SAMPLE COLLECTION THERMAL DESORBER

(71) Applicant: Lee Piper, Bushey, Watford, Hertfordshire (GB)

(72) Inventor: Lee Piper, Watford (GB)

(73) Assignee: Smiths Detection-Watford Limited, Hertfordshire (GB)

(*) Notice: Subject to any disclaimer, the term of this patent is extended or adjusted under 35 U.S.C. 154(b) by 0 days.

(21) Appl. No.: 14/430,175

(22) PCT Filed: Sep. 20, 2013

(86) PCT No.: PCT/GB2013/052475
§ 371 (c)(1),
(2) Date: Apr. 30, 2015

(87) PCT Pub. No.: WO2014/045057
PCT Pub. Date: Mar. 27, 2014

(65) Prior Publication Data
US 2015/0249001 A1    Sep. 3, 2015

Related U.S. Application Data

(60) Provisional application No. 61/704,420, filed on Sep. 21, 2012.

(51) Int. Cl.
*G01N 1/02*    (2006.01)
*H01J 49/04*    (2006.01)
(Continued)

(52) U.S. Cl.
CPC .............. *H01J 49/049* (2013.01); *G01N 1/02* (2013.01); *G01N 1/44* (2013.01); *G01N 27/622* (2013.01);
(Continued)

(58) Field of Classification Search
None
See application file for complete search history.

(56) References Cited

U.S. PATENT DOCUMENTS 5,083,019 A * 1/1992 Spangler .............. G01N 1/2247
                                                    250/282
5,476,794 A * 12/1995 O'Brien .................. G01N 1/02
                                                    422/534
(Continued)

FOREIGN PATENT DOCUMENTS

CA    2285153 A1    4/2000
CN    1701233 A    11/2005
(Continued)

OTHER PUBLICATIONS

Office Action dated May 24, 2016 for Chinese Application No. 201380049484.2.
(Continued)

*Primary Examiner* — Michael Logie
(74) *Attorney, Agent, or Firm* — Advent, LLP

(57) ABSTRACT

A thermal desorption apparatus is configured to detect a substance of interest in a sample, the apparatus comprising: a wand configured to support a swab and a detector comprising an analyser arranged to detect a substance of interest, wherein the wand is configured to couple to the detector such that thermal desorption of a sample from the swab provides a part of the sample to the analyser.

6 Claims, 10 Drawing Sheets

US 9,953,820 B2
Page 2

(51) Int. Cl.
*G01N 33/22* (2006.01)
*G01N 1/44* (2006.01)
*G01N 27/62* (2006.01)
*H01J 49/40* (2006.01)

(52) U.S. Cl.
CPC ............ *G01N 33/227* (2013.01); *H01J 49/40* (2013.01); *G01N 2001/028* (2013.01)

(56) References Cited

U.S. PATENT DOCUMENTS

| | | | | |
|---|---|---|---|---|
| 5,859,375 | A * | 1/1999 | Danylewych-May | ... G01N 1/02 73/863.21 |
| 5,988,002 | A | 11/1999 | Ludmila et al. | |
| 7,047,829 | B2 | 5/2006 | Napoli | |
| 7,594,447 | B2 | 9/2009 | Napoli | |
| 7,947,949 | B2 | 5/2011 | Chen et al. | |
| 8,528,425 | B2 | 9/2013 | Wang et al. | |
| 2005/0019220 | A1* | 1/2005 | Napoli | ..................... G01N 1/02 250/288 |
| 2005/0058575 | A1* | 3/2005 | Ishikawa | .............. G01N 1/2214 422/83 |
| 2007/0137319 | A1* | 6/2007 | Nacson | .................... G01N 1/02 73/864 |
| 2008/0101995 | A1* | 5/2008 | Gabowicz | ........... G01N 27/622 422/400 |
| 2008/0250877 | A1* | 10/2008 | Wu | .......................... G01N 1/14 73/864.33 |
| 2008/0314546 | A1* | 12/2008 | Banhart | ................ B22F 3/1103 164/61 |
| 2009/0249897 | A1* | 10/2009 | Doring | ..................... G01N 1/02 73/864.71 |
| 2010/0019140 | A1* | 1/2010 | Amirav | ................. H01J 49/049 250/282 |
| 2011/0223674 | A1 | 9/2011 | Robert et al. | |
| 2011/0259127 | A1* | 10/2011 | Beer | ....................... G01N 1/02 73/863.11 |
| 2011/0290041 | A1 | 12/2011 | Wang et al. | |
| 2014/0069477 | A1* | 3/2014 | Haider | ................... H01L 35/30 136/205 |

FOREIGN PATENT DOCUMENTS

| | | | | |
|---|---|---|---|---|
| EP | 0992782 | | 4/2000 | |
| EP | 1434050 | | 6/2004 | |
| GB | 2458374 | A * | 9/2009 | ............... G01N 1/02 |

OTHER PUBLICATIONS

International Search Report for PCT/GB2013/52475 dated Jan. 28, 2014.

Office Action dated Jul. 4, 2017 for Japanese Appln. No. 2015-532506.

* cited by examiner

SAMPLE COLLECTION THERMAL DESORBER

The present disclosure relates to methods and apparatus for the detection of substances of interest. More particularly the disclosure relates to methods and apparatus for the thermal desorption of samples for example to enable analysis to detect substances of interest in the samples. Analysis may be performed using spectrometers, such as ion mobility spectrometers and/or mass spectrometers.

In facilities such as airports and venues where large numbers of people may gather, there is a need to detect traces of substances of interest such as explosives and illegal drugs.

Embodiments of the present disclosure will now be described, by way of example only, with reference to the accompanying drawings in which:

FIG. 1, and FIG. 1A, 1B, 1C and 1D show various views of a wand and detector;

Figure 1:
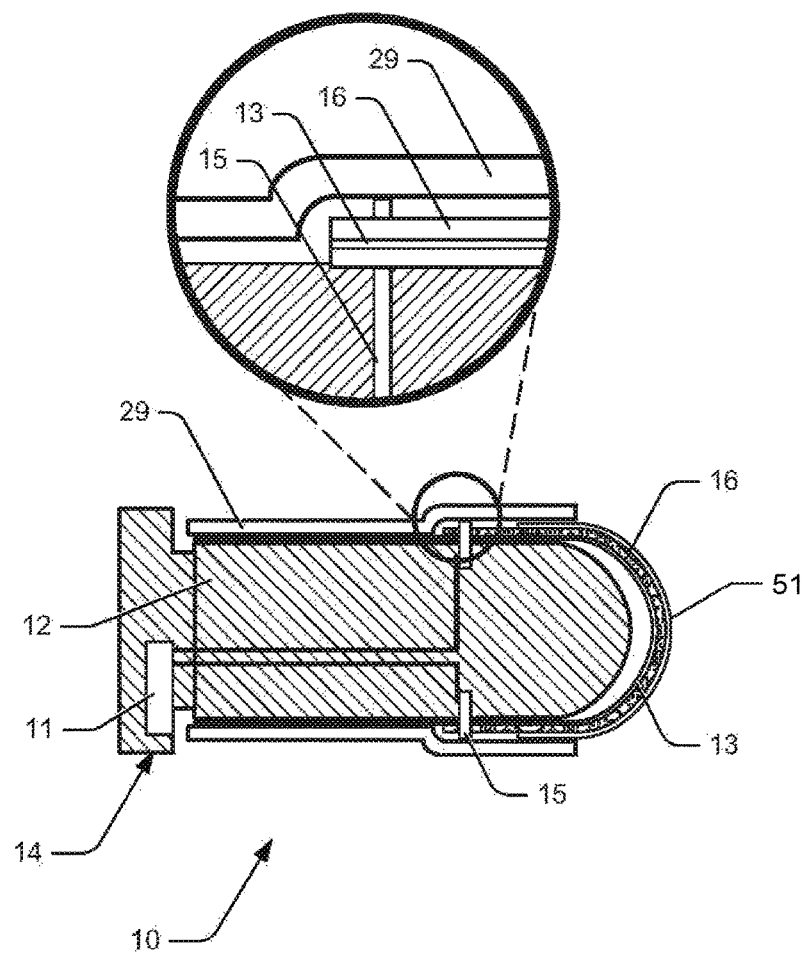
FIG. 1A shows a section of an apparatus for sample collection and analysis in a first configuration.
FIG. 1B shows the apparatus shown in FIG. 1A in a second configuration, and includes an inset to illustrate detail of certain features of the apparatus.
FIG. 1C is a perspective view of an apparatus for sample collection and analysis indicating insertion of a wand into a detector.
FIG. 1D is a perspective view of a wand in accordance with an embodiment of the disclosure.

To detect substances of interest carried on an article, the article can be swabbed to collect a sample, thermal desorption of parts of the sample from the swab facilitates the detection of substances of interest in the sample.

In one aspect, a thermal desorption apparatus comprises a wand configured to support a swab and a detector comprising an analyser arranged to detect a substance of interest. The wand is configured to couple to the detector such that thermal desorption of a sample from the swab provides a part of the sample to the analyser. The thermally desorbed parts of the sample may be analysed to detect the presence of substances of interest in the collected sample. Thus, there is no need to remove a swab from a wand and separately arrange that swab in a detector, and this may make the detection process more efficient.

In one aspect, a sample collection wand comprises, a wand body arranged to enable manipulation of the wand, a swab support coupled to the wand body that is arranged to support a swab spaced from the wand body so the swab and swab support are thermally insulated from the wand body. The wand or the detector may comprise a heater.

In an embodiment, the wand is arranged to thermally insulate the swab from the wand, for example the wand may comprise a swab support spaced from the wand to thermally insulate a supported swab. The thermal insulation may be provided by a spacing, which may comprise an air gap. Thermal insulation between the swab and the wand inhibits the transfer of heat to the body of the wand and so reduces the heat capacity of the mass to be heated when thermally desorbing the sample. This may reduce the power used to heat the swab and may also promote rapid heating and/or cooling of the wand, such as in comparison to a system in which the components are in contact. Where heating is performed more rapidly, this may provide the thermally desorbed (for example volatilised) sample to the analyser in a higher temporal concentration (e.g., dose per unit time). This may enable battery operated detectors to improve sensitivity without compromising battery life. This may facilitate the provision of manually portable detection apparatus and, some examples of the disclosure provide a hand held detector.

In an embodiment, the swab support is movable with respect to the wand to enable the swab support to be pressed toward the wand to reduce the spacing. For example, the swab support is flexible. This may enable the body of the wand to provide additional support for the swab as it is rubbed on an article to collect sample, so a light weight (and hence low heat capacity) swab support can be used and this may further facilitate rapid heating.

In an embodiment, the swab support is configured so, after it has been moved to reduce the spacing, it tends to return toward a position in which the swab support is spaced from the wand, for example the swab support may be resilient. Thus, an operator need not take specific action to ensure the swab is properly supported when swabbing, or properly insulated when heating.

In an embodiment, the wand may comprise a heater for heating the collected sample. Where the wand includes a swab support the heater may be included in the swab support or function as the support. This facilitates heat transfer to the sample. In some embodiments, the apparatus further comprises the swab.

In one aspect, a thermal desorption swab support comprises a resilient laminar strip comprising a heater arranged to heat the swab support for thermal desorption of a sample. In an embodiment the resilient laminar strip comprises at least one polymeric layer. The heater may comprise a conductive track coupled to the polymeric layer. In an embodiment the polymeric layer comprises polyimide. In an embodiment, the heater is arranged between two polymeric layers. In an embodiment, the thermal desorption swab support comprises first and second couplings adapted to enable the swab support to be mechanically coupled to first and second couplings of a thermal desorption and sample collection wand, and in which at least one of the couplings is arranged to provide electrical coupling to the heater.

In an aspect, a detector comprises an analyser for detecting a substance of interest in a thermally desorbed sample, and a wand coupling for coupling the detector to a sample collection wand to provide a path for a thermally desorbed sample from the sample collection wand to the analyser. In an embodiment, the wand coupling further comprises an electrical coupling adapted to electrically couple the detector with said wand. In embodiments, the wand coupling and the electrical coupling are arranged so when said sample collection wand is positioned to provide a sample to the analyser, the electrical coupling provides electrical contact with an electrical coupling of said sample collection wand.

FIG. 1 shows schematic views of an example of a thermal desorption apparatus 1 comprising a wand 10 for collecting samples and a detector 20 for detecting substances of interest in collected samples.

Figure 1A:
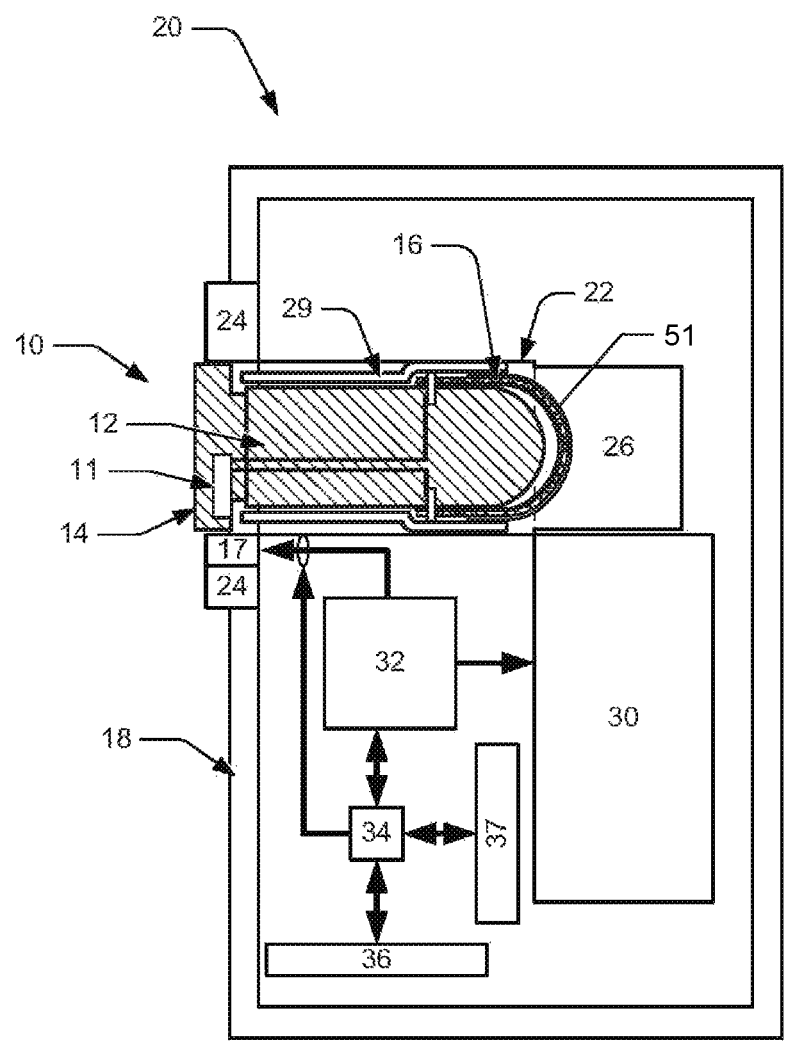
Figure 1B:
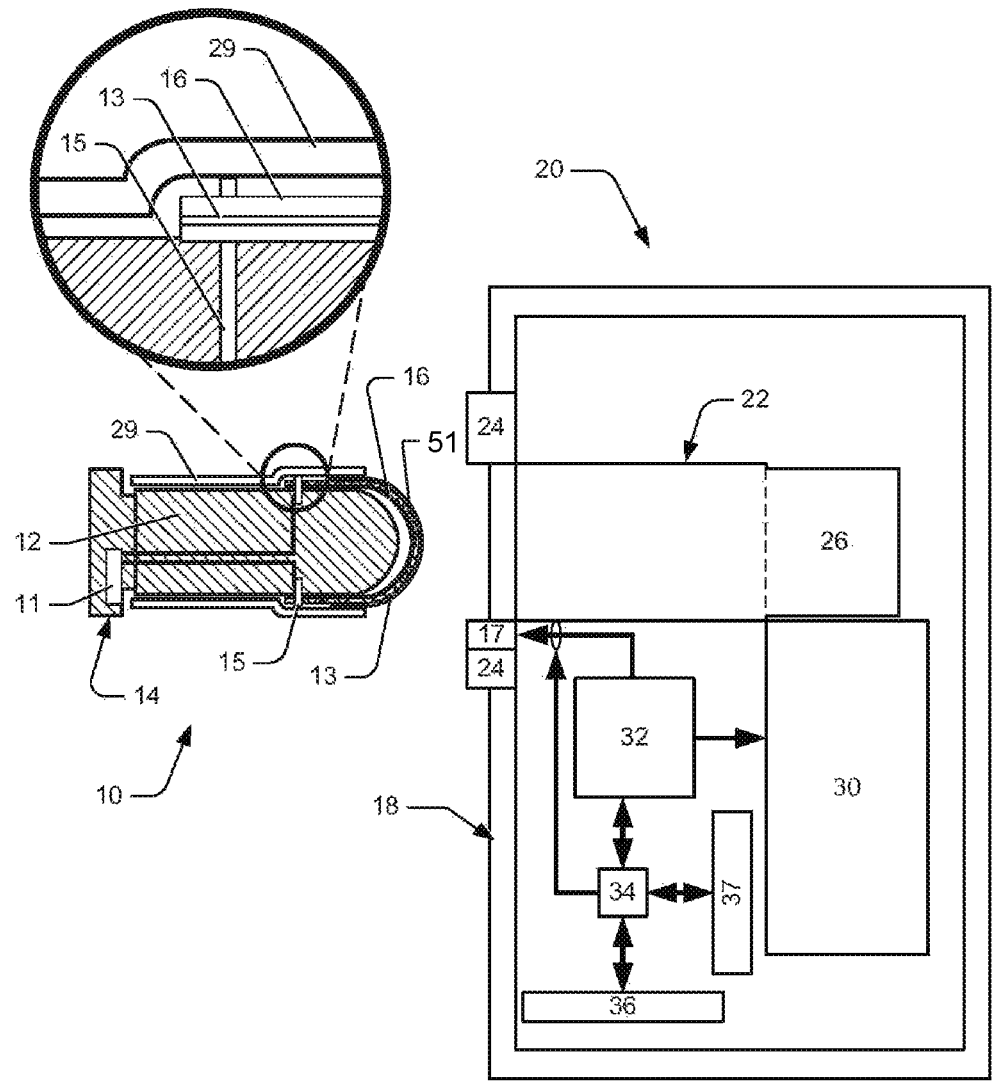

The views shown in FIG. 1A and FIG. 1B correspond to two configurations of the wand 10 and detector 20. FIG. 1A shows the wand 10 inserted into the detector 20; and FIG. 1B shows the wand 10 separated from the detector 20. In the Figures, like reference are used to indicate like elements.

The wand 10 shown in FIG. 1 comprises a wand body 12 and a swab support 16 for supporting a swab 51. In an embodiment, the swab support 16 is arranged to thermally insulate the swab 51 from the wand body 12, for example by spacing the swab 51 from the wand body 12. The spacing may comprise an air gap. To provide the spacing, the swab support 16 can be bowed out from the wand body 12. Alternatively or additionally the swab support 16 may be spaced from the wand body 12 by spacers that hold the swab support 16 away from the body 12. Alternatively or additionally, the wand body 12 may comprise a recess arranged behind the swab support 16 to provide spacing between the swab support 16 and the wand body 12. Alternatively or additionally a thermal insulator such as expanded polystyrene, a fleece, polymeric foam (for example an open cell foam material), a chamber of gas (for example gas at reduced pressure), or an evacuated chamber may be disposed between the swab support 16 and the wand body 12. Other thermal insulation materials may be used to thermally insulate the swab support 16 from the wand body 12 may reduce the heat capacity of the arrangement that needs to be heated. In some examples, the wand body 12 may comprise a thermally reflective surface (for example, a silvered surface) arranged behind the swab support 16 to reflect heat back on to the swab support 16.

The swab support 16 may be coupled to the wand body 12 for example by the swab support 16 being integrally formed with the wand body 12, or by a separate swab support 16 being joined to the wand body 12. In FIG. 1, the swab support 16 is shown as being coupled at two locations 15, 15' to the wand body 12, however a greater or smaller number of couplings may be used. Where the swab support includes a heater 13 the couplings 15, 15' may provide electrical coupling to the heater 13.

The swab support 16 shown in FIG. 1 may be movable with respect to the wand body 12 so in use it can be deflected against the wand body for swabbing (for example closing the spacing). For example, the swab support may be movable between a heating configuration in which the thermal insulation between the swab support 16 and the wand body 12 is relatively more effective, and a collection configuration where the mechanical support provided by the wand body is relatively more robust. Being movable may comprise the swab support 16 being flexible, for example the swab support 16 may comprise one or more flexible members and/or it may be hinged, pivoted, or otherwise flexibly coupled to the wand body 12.

The swab support 16 shown in FIG. 1 may be resilient. For example, it may be configured so, after it has been pressed against the wand body when swabbing, the swab support will tend to restore the spacing between the swab support 16 and the wand body 12. This function may be provided by at least a part of the swab support comprising resilient material. In some cases, resilience may be provided by biasing, for example using a separate arrangement configured to bias the swab support to restore the spacing after the swab support has been deflected. Examples of structures for biasing include springs, elastic members, and mechanical, magnetic, or electromechanical biasing.

The wand 10 shown in FIG. 1 includes a heater 13 for heating a sample collected on a swab 51. The heater 13 may be part of the swab support 16. In an embodiment, the heater 13 is an electrical conductor arranged to heat by resistive heating. For example, the heater may be formed of resistive material selected to heat the substance of interest to cause at least a portion of it to enter a vapour phase. The heater 13 may comprise an electrically conductive track to provide a resistive heating element. The heater 13 can be at least partially covered with an insulator, such as a thermal insulator, and/or a dielectric type material on one or both sides, (for example, a polymeric layer). For example, an electrically conductive track may be sandwiched between two layers of an electrical insulator/dielectric. Other appropriate insulator/dielectric materials exhibiting similar properties may be used. Polyimide, for example Kapton (RTM), is one example of a material that is suitable for this purpose due to its thermal and mechanical properties and inertness. The electrically conductive track may comprise a metal, such as an alloy of nickel and chromium, for example nichrome. The electrically conductive track can be glued, deposited, or otherwise bonded onto the insulator/dielectric, or may be clamped or laid/assembled on to it, such as thorough use of a collar that friction fits with a portion of the wand body 12. A sleeve 29 may surround the wand 10 and may partially cover the swab support 16.

The wand 10 shown in FIG. 1 may include an engagement feature 14 for mechanically engaging with a wand fitting 24 of the detector 20. The engagement feature 14 may comprise an electrical coupling 11 to provide electrical contact between the heater 13 and the detector 20. For example, a portion of the wand body 12 is shaped to engage with an interior surface so as to secure or at least partially secure the wand to the detector 20. In other examples, the mechanical engagement is achieved by employing a securing device, such as a deformable clamp type structure configured to hold the wand in place but allows for withdrawal of the wand upon sufficient outward force is applied (e.g., the wand releases when a user pulls on the wand).

Turning now to the detector 20, the detector 20 shown in FIG. 1 comprises an analyser 30 configured to detect substances of interest in a thermally desorbed sample. The analyser 30 is coupled to an inlet 26 for receiving a sample to be analysed. The analyser 30 may comprise a spectrometer, such as an IMS spectrometer as described below with reference to FIG. 2.

The detector 20 may comprise a housing 18 having a port 22 for receiving a wand 1 to enable the wand to provide a sample to the analyser 30. In embodiments the detector 20 comprises a wand fitting 24 configured to couple with a wand 10. The wand fitting 24 may be configured to engage with the engagement feature 14 of the wand 10 to positively locate the wand in position. The wand fitting 24 of the detector 20 may comprise an electrical coupling 17 configured to provide electrical contact with the electrical coupling 11 of the wand 10 when the wand is located in a selected position, for example, a position selected to provide a sample to the analyser 30.

The port 22 may be configured to enable the wand to be inserted into the detector. The wand fitting 24 may be arranged on the interior of the port, for example, at the mouth of the port 22. This permits the introduction of sample from the swab 51 without having to dissemble the wand (whether fully or partially) and without removing the swab from the wand to permit sample introduction.

Inserting the wand into the port 22 is one example of coupling the wand 10 to the detector 20 to provide a path from the sample to the analyser. The wand 10 need not be inserted, but may be coupled to the outside of the detector, for example the wand may be joined to the housing 18 and need not be inserted into it.

The features described with reference to the port 22 (and those features described in combination with the port 22) may be applied to any coupling that couples the detector 20 to the wand 10 to provide a path from the swab support 16 to the analyser 30. The path between the swab support of the wand and the analyser may be arranged to exclude contaminants from the analyser 30. In some examples, a filter is provided which assists in excluding contaminants from the analyser 30.

The port 22 and the wand 10 and/or wand fitting 24 may be configured to cooperate with each other to close the detector when the wand is inserted into the port 22. For example, the wand fitting 24 may comprise a protrusion arranged so when the wand 10 is inserted into the port 22, the protrusion acts as a lid or cap to close the port 22. In one example, the port and wand may comprise complementary features arranged such that when, in use, the wand 10 is inserted into the port the complementary features cooperate to enclose the swab support in the detector. This enclosure may be arranged so air can be drawn into the detector but the thermally desorbed sample is inhibited from escaping.

The detector 20 may comprise a power provider 32 configured to provide power to components of the detector and/or to the wand via electrical coupling 17. The detector 20 may also comprise a controller 34. In embodiments, the controller 34 is coupled to a communications interface 37 to enable the controller to send and/or receive data to/from a remote device, for example via a wired or wireless communications link. The controller 34 may be coupled to a user interface 36 to receive operator input/commands from the user interface 36, and/or to output information to the operator.

In operation, a swab 51 may be disposed on the swab support 16 so the swab 51 is spaced from the wand body 12. The wand 10 may be manipulated by an operator so the swab 51 is rubbed on an article to be tested, and substances carried on the article may become deposited on the swab 51. Where the swab support 16 is flexible, pressing the wand on to the article may deform the swab support 16 and press the swab support against the body 12 of the wand 10. Thus, the body 12 of the wand 10 may provide mechanical support to enable the swab 51 to be rubbed robustly against the article to collect a sample.

After swabbing, the wand may be inserted into a port 22 of the detector 20 so the swab support 16 and the swab 51 provide the sample to the inlet 26. The engagement feature 14 of the wand 10 may engage with the wand fitting 24 of the detector 20. With the wand in place, the electrical coupling 17 of the detector 20 may contact the electrical coupling 11 of the wand 10 to enable the provision of power to the heater 13.

In examples, in response to a control signal entered via the user interface 36, the controller 34 controls the heater 13 to heat to a selected temperature to thermally desorb part of the sample from the swab. The thermally desorbed sample may pass from the inlet 26 into the analyser 30. The analyser 30 can analyse the sample to detect substances of interest which may be present in the sample. Data representative of the analysis can be passed from the analyser to the controller 34. In the event that a substance of interest is detected by the analyser 30, the controller 34 can control the user interface 36 and/or the communications interface 37 to signal that a substance of interest has been detected. If a substance of interest is detected, the operator may replace the swab to avoid contamination of subsequent tests.

Once a test is complete, the controller 34 may control the heater 13 to heat the sample to a bake-off temperature selected to vaporise residue remaining on the swab after testing. The temperature selected for testing, and the temperature selected to bake substances off the swab may be selected based on which substances are of interest.

The controller 34 may be provided by any appropriate control logic such as an FPGA, an ASIC, a general purpose processor, or an appropriate arrangement of logic gates. The detection apparatus 1 may comprise non-transitory data storage (e.g a volatile or non-volatile memory), storing program instructions configured to program the controller to operate according to any method described herein.

In some examples the controller 34 comprises a memory storing a plurality of pre-set temperature control settings, and the user interface is configured to enable a user to select a particular setting. For example, the user interface may enable a user to select settings configured for particular groups of compounds, for example "Narcotics", or "Explosives", or subgroups thereof. In these examples, the controller 34 is configured to receive a control signal from the user interface 36 based on the selected setting, and to control the temperature of the heater 13 based on the selected setting. Alternatively or additionally, the user interface may be configured to enable the user to simply select a temperature, and the controller 34 can be configured to heat the heater to this selected temperature.

In some examples, the controller 34 may be configured to control the heater 13 to heat the sample to a first selected temperature for a first time interval so as to thermally desorb a first selected group of substances. The controller 34 may then control the heater 13 to further raise the temperature to a second selected temperature for a second time interval so as to thermally desorb a second group of substances, different from the first group. This may enable separate groups of compounds to be tested for separately, for example to provide improved resolution in the detector. The use of a light weight (low thermal mass) swab support, and thermal insulation may facilitate temperature control of this kind. Additional temperatures and time intervals may be added to this cycle. For example, the controller may be configured to initiate a bake-off interval, during which the heater is heated to a temperature selected to thermally desorb residue from the swab.

Controlling the heater may comprise controlling the provision of power to the wand, or it may comprise providing control signals to the wand to switch the heater on or off, and/or a temperature control signal to cause heating to a selected temperature. In some cases the controller may be configured to control the heater based on the temperature of the heater, but in some cases the controller need not perform temperature control as the wand itself may be configured to provide temperature control.

The controller 34 can be configured to maintain a selected temperature for a selected time interval. For example the temperature, and/or the time interval may be selected based on the substance of interest.

The user interface 36 may include user operable controls to input commands to the controller 34 and an output to provide indications to the user regarding operation of the detector. The output may include a display, or one or more visual indicators. The communication interface 37 may comprise a wired and/or wireless communication interface such as an Ethernet, USB, WI-FI(RTM), IEEE-802.11, GSM, GPRS, HSDPA or other communications interface for sending and receiving information. The detector may be configured to relay data based on analysis of a sample from the analyser 30 to a remote device via the communications interface 36.

Examples of power providers 32 include batteries, fuel cells, and capacitors. In some cases the power provider may comprise a transformer or adapter configured to derive power from an external power supply such as an alternating current, AC, mains supply. In these examples the power provider may include a power store and a charger adapted to charge/recharge the power store. In some cases the wand comprises a power provider, and the controller need only provide control signals to the wand. Where both detector and wand comprise power providers the power provider of one or other of the wand and detector may be used as back-up or auxiliary power.

Figure 1C:
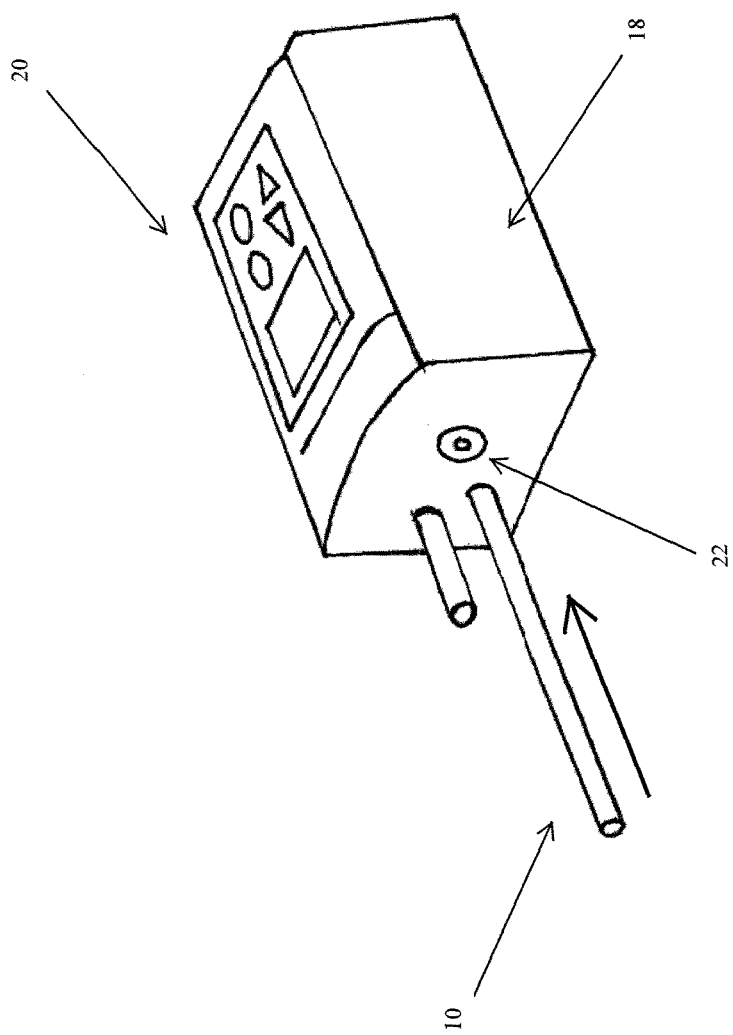

FIG. 1C shows an embodiment of a wand that is configured to insert into a port 22 defined by a housing 18 of a detector 20. In the illustrated embodiment, a portion of the wand can be received in the port. In operation, insertion of the wand 12, e.g., a portion including a swab/swab support 16, may trigger a heater included in the wand to heat a least a portion of any substance of interest that may be captured on an included swab. Various mechanisms can be used to trigger operation of the heater, examples include, but are not limited to, electrical contact systems, optical sensors, physical contact switches (e.g., a switch, such as a toggle switch disposed adjacent an opening of the port 22).

The portion of the housing 18 that defines and/or is adjacent the port can be configured to support the wand and/or to hold it in alignment with the port to maximize the likelihood that vapour from the substance of interest is drawn into the detector. While a pneumatic seal may be formed between the wand body 12 and the housing 18, in other embodiments, the wand 10 and housing 18 are configured so at least some ambient air is drawn into the port and/or detector so as to avoid a vapour lock situation in which a vapourized sample cannot be drawn into the detector due to existence of a pneumatic type seal.

In some embodiments, waste heat from the detector's components may be implemented to aid in vaporizing the sample and so forth. For instance, a fan used to cool the detector's components may cause an interior portion of the port to be warmer than ambient temperature without interfering in sample introduction.

Figure 1D:
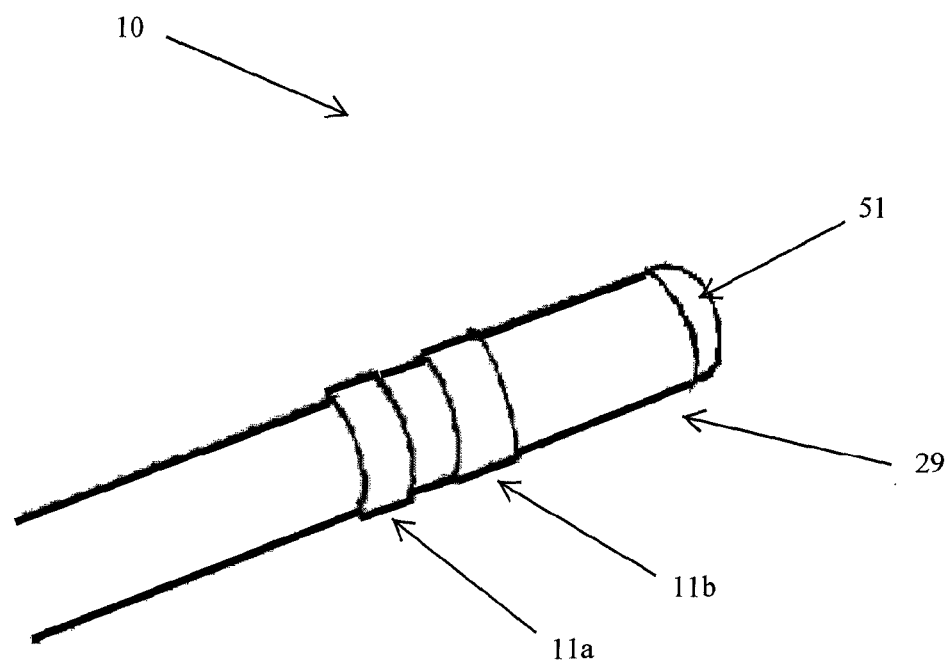

FIG. 1D shows a view of the wand. The wand may comprise an electrical coupling 11a, 11b for coupling electrical power to the heater, wherein the coupling is arranged to electrically couple with the detector when the wand is coupled to the detector. In the illustrated embodiment, the electrical couplings are ring shaped electrical couplings e.g., 11a and 11b and face outward from the wand. The electrical couplings are configured to engage with corresponding electrical contacts disposed on an interior surface of a port, such as port 22. The wand, including the electrical couplings 11a and 11b, can be configured so that as the wand is inserted in the port the electrical couplings contact the corresponding electrical contacts that, for example, can provide electricity for the heater and/or physically secure the wand in the port 22. The electrical contact, for instance, are a flap or band of an electrically conductive material that can snap or friction fit with the ring electrical couplings. By forming the electrical couplings as exterior facing rings, the wand need not be aligned in comparison to a system in which electrical couplings are disposed on a side of the wand.

In embodiments, a sleeve 29 extends over at least a portion of an end of the wand 10. The sleeve 29 can be used to protect a swab support and or at least partially secure a swab 51 to the wand. For example, the sleeve 29 may thread on the want to clamp down on finger type structures used to hold the swab in position. This can permit efficient placement of the swab on the swab holder when changing swabs while securely hold the swab during sample collection and/or during sample introduction.

Figure 2:
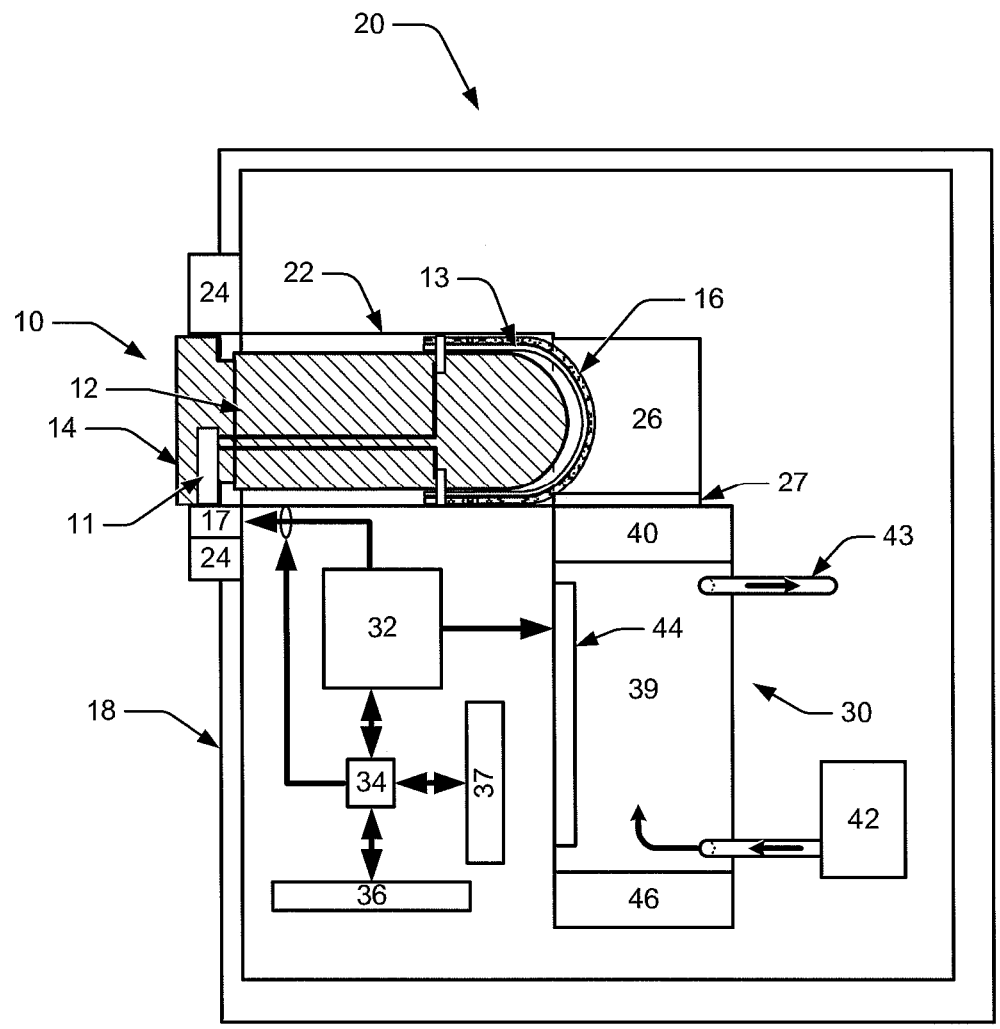
FIG. 2 shows a schematic view of a particular example of an apparatus for sample collection and analysis.

FIG. 2 shows a detector 20 which includes an analyser 30 (such as the analyser 30 shown in FIG. 1) which may comprise an ion mobility spectrometer. Other apparatus and methods may be applied to provide the analyser 30. For example, TOFMS, DMS, hybrid IMS-mass spectroscopy, and/or other analytical methods and/or apparatus may be used.

An ion mobility spectrometer may comprise an ioniser 40 configured to ionise a thermally desorbed sample. The ioniser 40 may be arranged between the inlet 26 and the drift chamber 39 so a sample passed into the inlet can flow through the ioniser 40 to reach the drift chamber 39. A filter 27 may be provided between the inlet 26 of the analyser 30 and the ioniser 40.

An electric field applier 44 may be coupled to the power provider 32 to apply an electric field to the drift chamber 39 to accelerate ions along the drift chamber 39 toward an ion detector 46. In embodiments a drift gas supply 42 is coupled to provide a flow of drift gas along the drift chamber 39 to a gas exhaust 43. The gas exhaust 43 may be arranged toward the other end of the drift chamber 43 from the gas supply to enable drift gas to flow out of the drift chamber 39. In embodiments the flow of drift gas may oppose a flow of ions from the ioniser 40 toward the ion detector 46.

A swabbed sample may be provided on the swab support 16 of the wand 10 as described above with reference to FIG. 1. With the wand 10 in place, the electrical coupling 17 of the detector 20 may provide electrical contact with the electrical coupling 11 of the wand 10 to enable the provision of power to the heater 13. A control signal from the user interface 36 may cause the controller 34 to control the drift gas supply 42 to provide a flow of gas along the drift chamber 39 at a selected flow rate. The controller 34 may then control the heater 13 on the wand 10 to heat the sample to a selected temperature. In embodiments, the thermally desorbed sample can pass into the inlet 26 and through the filter 27 into the ioniser 40. The ioniser 40 can ionise the thermally desorbed sample for analysis.

The controller 34 may control the electric field applier 44 to apply a selected potential difference along the drift chamber 39 so as to accelerate ions along the drift chamber 39 toward the ion detector 46 against the flow of drift gas. As will be appreciated, based on the flow rate of the drift gas, the electric field applied along the drift chamber 39, and the length of the drift chamber 39, the arrival time of ions at the detector 46 of this second embodiment can provide an indication of characteristics of the ions. This may enables substances of interest (for example explosives or controlled drugs) to be identified in the sample based on known characteristics of these substances. The identification may be performed at the controller 34, or data may be relayed from the controller 34 to the operator via the user interface 36, or to a remote device via the communication interface 37.

The ioniser 40 may comprise a discharge arc or another source of ionising radiation. The electric field applier 44 may comprise one or more electrodes, for example a series of electrically conductive frames or rings, disposed about the periphery of the drift chamber 39, and distributed along its length. Thus, applying a potential difference to the electric field applier 44 sets up an electric field along the drift chamber. By way of example the apparatus shown in FIG. 2 is shown as having a single drift chamber 39. However, in some cases two drift chambers may be used, one to analyse positively charged ions, and a second chamber to analyse negatively charged ions. The controller 34 may be configured to apply an alternating voltage to the field applier 44 so as to vary the field conditions in the drift chamber so a single chamber may be used for the analysis of both positive and negative ions.

The filter 27 may be configured to permit a selected group of substances to pass into the analyser, but to exclude others. For example, on the basis of particle size. For example, the filter 27 may be configured to be selectively permeable, for example to permit vapour to pass into the inlet, but to exclude particles over a selected size such as dust. The filter may comprise a selectively permeable material, for example a membrane and/or a mesh.

FIG. 3 shows three views of an embodiment of a wand 10. FIG. 3A shows a plan view looking down onto the wand at the swab support 16. FIG. 3B shows a section of the wand along the line B-B indicated in FIG. 3A, and FIG. 3C shows a section of the wand along the line C-C indicated in FIG. 3A. The wand 10 shown in FIG. 3 corresponds to the wand shown in FIGS. 1 and 2 and like reference numerals are used to indicate like elements.

In FIG. 3, the body of the wand 10 is elongate to facilitate manipulation by a user, and this may enable the wand 10 to be inserted into a port 22 of a detector such as detector 20 shown in FIGS. 1 and 2. The swab support 16 may comprise a resilient laminar strip extending from a coupling 15 on a lateral surface of the wand body 12, over its tip 12', to a second coupling 15'. The length of the strip may be selected so the swab support 16 is spaced from the tip 12' of the body 12 as discussed above with reference to FIG. 1.

The sleeve 29 shown in FIG. 3 may include an aperture 29' arranged over the tip 12' of the wand to expose the swab support 16. For example, the sleeve 29 may be configured to capture a peripheral portion of a swab. For example, the sleeve includes an internal thread that engages with a corresponding threading on the wand body to secure the swab to the wand and/or at least partially protect the swab support and so forth. In embodiments, a swab is formed in a cup shape or partial cup shape (such as a swab strip that is formed with a curvature) to conform to the swab support. In this fashion, the swab may remain in contact with the swab support such as during sample collection and/or thermal desorption. In embodiments, the wand is configured so that a swab can be placed on the wand without a user having to physically place the swab on the swab support. For example a dispenser is provided so that insertion of the wand can result in the swab being placed on the swab support. This allows placement of the swab without a user having to "glove-up" to place the swab without causing contamination. In the aperture, the side edges of the swab support 16 may be bounded by ridges 52. The wand 10 may comprise a temperature sensor 50 in thermal contact with the swab support 16 and coupled to the electrical coupling 11 to provide an indication of temperature to a controller, for example to the controller 34 of the detector 20 shown in FIGS. 1 and 2.

In FIG. 3 the wand 10 comprises a temperature sensor 50. A thermocouple or a thermistor or any other temperature sensitive element may be used for this purpose. However, as the resistance and heat capacity of the swab support and swab can be known in advance, in some examples the controller 34 (in FIG. 1 & FIG. 2) can control the temperature of the swab support 16 simply by providing a selected power for a selected duration. Alternatively or additionally, the controller 34 may be configured to sense the temperature of the swab support 16 based on the impedance (for example electrical resistance) of the heater 13 and to control heating based on the sensed temperature. Other methods of temperature sensing and control may be applied.

Figure 3A:
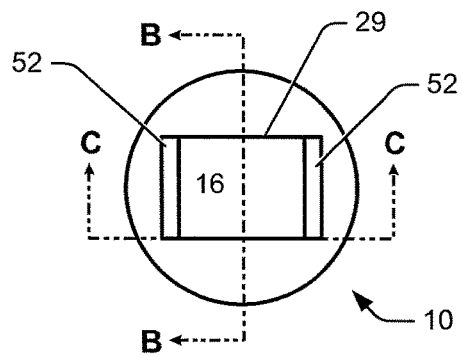
FIG. 3A shows a plan view of a wand for use with the apparatus shown in FIGS. 1 and 2.
Figure 3B:
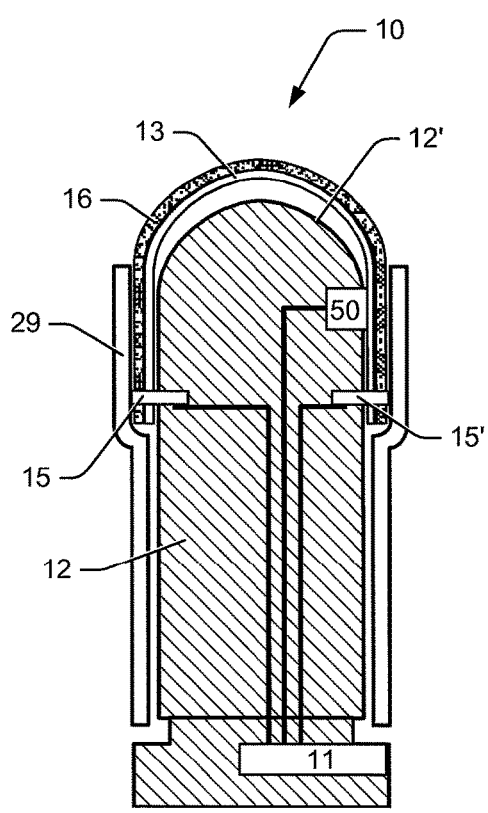
FIG. 3B shows a section of the wand along the line B-B indicated in FIG. 3A.
Figure 3C:
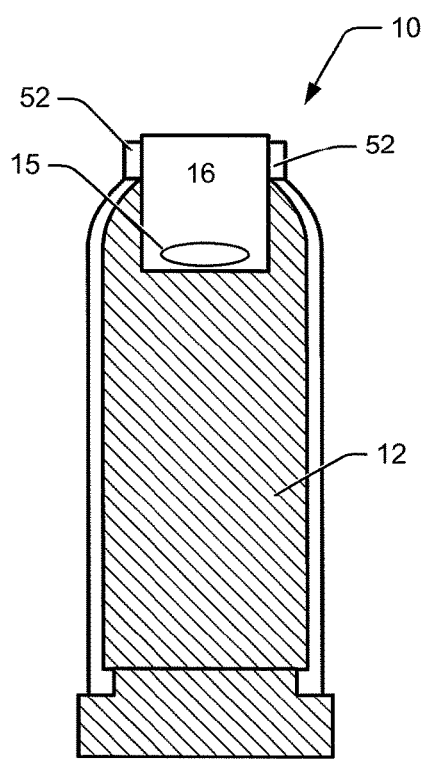
FIG. 3C shows a section of the wand along the line C-C indicated in FIG. 3A.
Figure 3D:
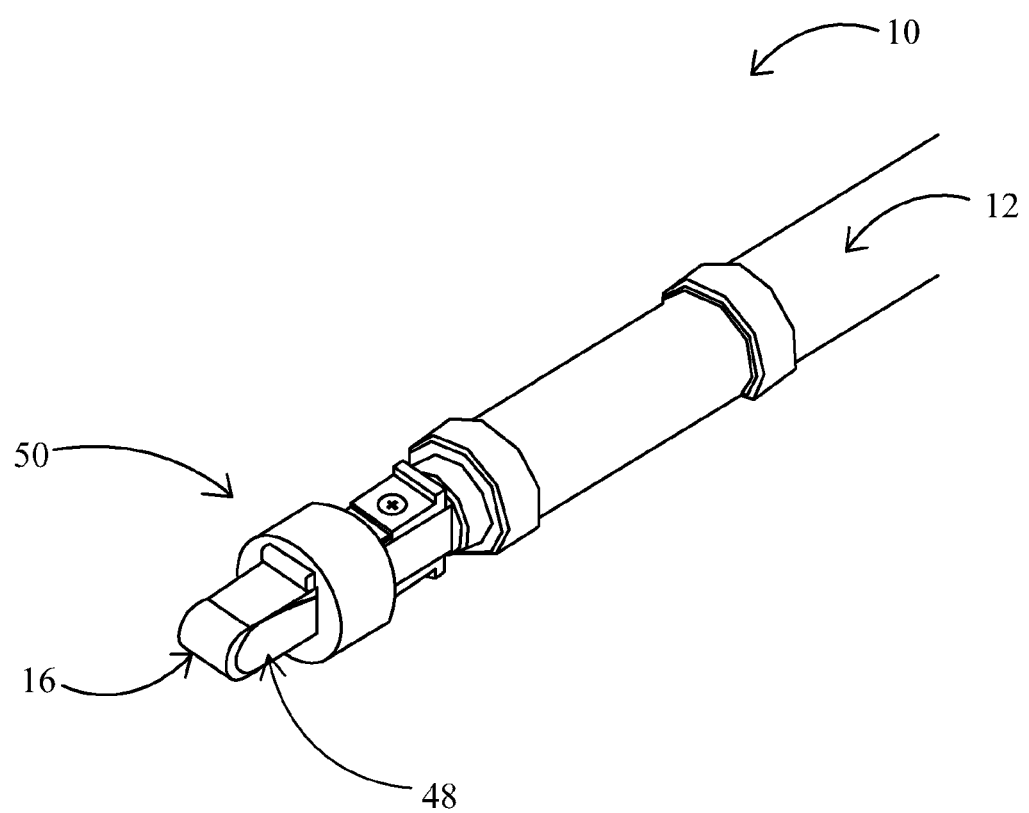
FIG. 3D shows a wand in accordance with an embodiment of the present disclosure.

FIG. 3D illustrates various components of a wand 10 in accordance with embodiments of the present disclosure. A swab support 16 is disposed at the end of the wand body 12. Adjacent the swab support 16, as illustrated, is a finger structure 48. In examples, two generally opposing finger structures are disposed on opposite side of the swab support.

The finger structure can include a flared end that angles away from the support. The flared end may assist in capturing a swab, such as dispensed from a dispenser, when placing the swab on the wand. The finger structure in examples, is at least partially deformable so that it deforms while capturing a swab but then securely holds the swab. Swab placement, of course can be achieved without a user having to pick it up manually. The finger structure may be formed to support and/or prevent the swab structure from moving during sample collection. For example, when swabbing an article the finger may prevent the swab support from deforming. The finger structure can be held in place by a sleeve that engage with the wand body 12 through a friction fit, a threaded engagement, a detent/catch ball structure or the like securing configuration. The finger structure may be space apart from the swab support 16 so that it is not in thermal contact during sample introduction.

With continued reference to FIG. 3D, a gasket 50 can be included in the wand. In embodiments, the gasket 50 is a deformable gasket, such as formed of a semi-rigid rubber type material, or it can be formed of a plastic material. The gasket can be included to assist in securing the swab support 16 to the wand body 12. For example, the gasket is used to capture the swab support and end of clips that are use to secure the swab support to the wand body 12. In this manner, the clips can be secured, such as via respective screws, and the not secured ends of the clips and swab support are generally secured with the gasket. The gasket can serve other purposes as well, for example, it can align a sleeve to the wand body. A gasket can permit the non-secured end of the sleeve to flex slightly during sample collection while securing the swab and/or swab support from deflecting too much. The gasket can also assist in placing the swab on the swab support. The gasket, in embodiments, can have a cylindrical or frusto-conical shape that aids in capturing the swab and/or securing it during use.

Figure 4:
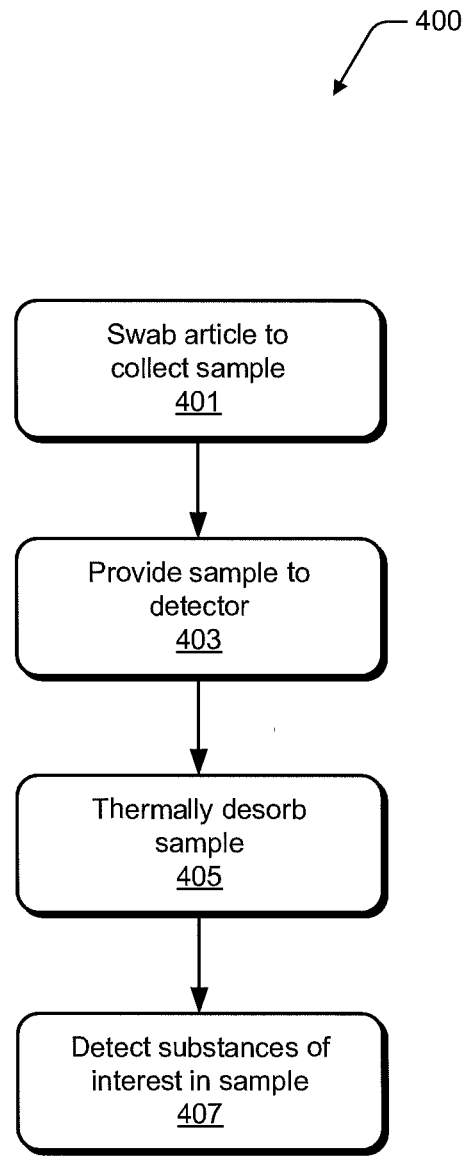
FIG. 4 depicts an operator using a hand held detection apparatus.

FIG. 4 illustrates a method 400 of detecting a substance of interest. The method may comprise a swabbing 401 in which an article is swabbed to collect a sample. The swab may be held on a wand, which may include a swab support. The swab support may be arranged to support the swab so it is thermally insulated from the wand.

The swab may then be provided 403 to a detector. Providing the swab to the detector may comprise coupling a wand to the detector, e.g by inserting the wand into the detector.

In embodiments the method comprises thermal desorption 405 in which the sample is thermally desorbed from the swab by heating the swab. The thermal desorbtion step may comprise a thermal insulation step in which the swab is thermally insulated from the detector and/or from the wand.

The method may further comprise detection 407 in which substances of interest may be detected in the thermally desorbed sample.

Figure 5:
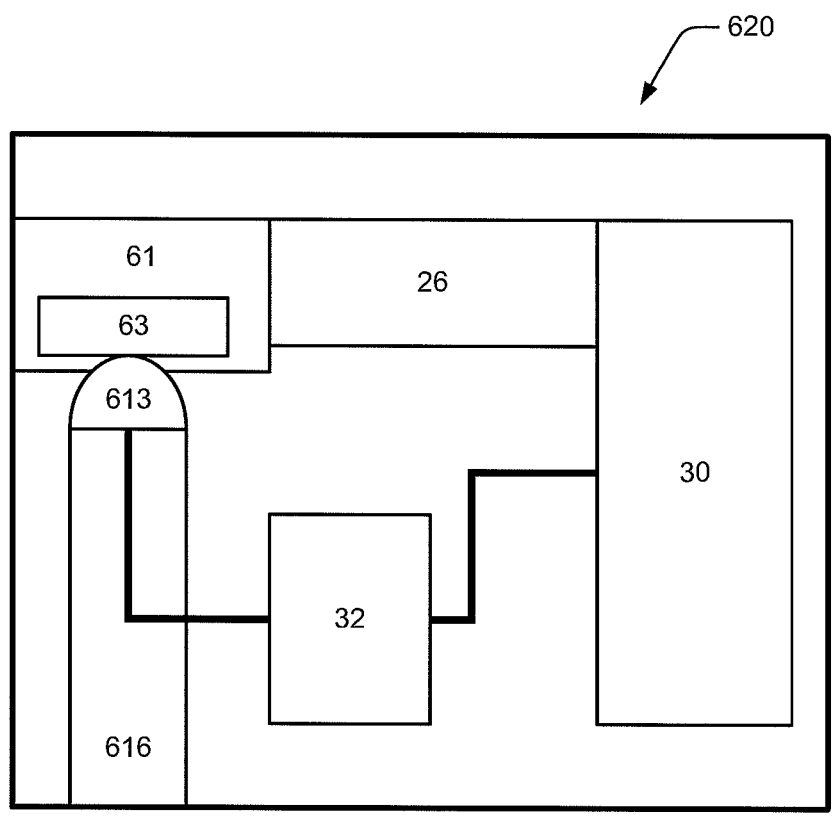
FIG. 5 depicts one arrangement of a detector.

FIG. 5 shows an example where a heater 613 is provided in a detector 620. As shown in FIG. 5 the heater 613 is disposed on a mounting 616. The detector 620 may further comprise a sample receiver 61 for receiving a sample 63 to be tested. The sample receiver 61 may be arranged adjacent an inlet 26 of an analyser 30. The heater 613 may be arranged for heating a sample 63 in the sample receiver 61 to thermally desorb substances from the sample to provide them to the inlet 26 for analysis by the analyser. The heater 613 may be arranged to be thermally insulated from the mounting 616 by spacing the heater 613 from the mounting 616.

In operation a swab carrying a sample 63 can be enclosed by the sample receiver 61. The power provider 32 may provide power to the heater 613 to thermally desorb the sample. The analyser 30 can analyse the thermally desorbed sample as described above with reference to FIGS. 1, 2 and 3.

The heater 613 may comprise a laminar structure such as described above with reference to the swab support 16 in FIG. 1, FIG. 2 and FIG. 3.

In the present disclosure, the term thermal desorption (and thermally desorb) includes heating to facilitate dispersal of solids and/or liquids, for example by dispersing them into a vapour, a gas, or a particulate dispersion Examples of thermal desorption include vaporisation, evaporation, volatilisation and sublimation.

Some analytical methods have been discussed. However the present disclosure has broader relevance. Samples may be analysed with an analyser 30 configured to detect substances of interest using any analytical method, including spectrometry methods such as ion mobility spectrometry, IMS, time of flight mass spectrometry, TOFMS, differential ion mobility spectrometry, DMS, and hybrid ion mobility spectrometry/mass-spectrometry methods and/or combinations of such methods.

As will be appreciated from the foregoing disclosure, a number of features of the wand, the detector and the heater may be used in combination. Many of these features are separable and useful in their own right and this is implicit in the disclosure. The following numbered embodiments provide examples of these combinations of features. These combinations are provided merely by way of example, other combinations are possible.

In a first embodiment the swab support comprises the heater provides an insulating spacing from the wand and is movable and resilient.

In a second embodiment the thermal desorption apparatus is arranged so coupling the wand to the detector arranges the swab support to provide a thermally desorbed sample to the analyser. The second embodiment may comprise the features of the first embodiment.

In a third exemplary embodiment the wand comprises an engagement feature arranged to couple the wand to the detector. The third embodiment may comprise the features of the first and/or the second embodiment.

In a fourth embodiment the detector comprises a wand fitting arranged so coupling the engagement feature to the detector enables the provision of electric power to the heater. The fourth embodiment may comprise the features of one or more of the first, second and third embodiment.

In a fifth embodiment the detector is configured so coupling the wand to the detector triggers the provision of electric power to the heater. The fifth embodiment may comprise the features of one or more of the first to fourth embodiments. In a sixth exemplary embodiment the controller is configured to control the heater based on the temperature of the swab support. The sixth embodiment may comprise the features of one or more of the first to fifth embodiments.

As has been made clear, the examples set forth above are only intended to illustrate the principles of the disclosure and should not be construed as limiting. Examples of the disclosure include kits of parts comprising one or more components of any of the apparatus described with reference to FIG. 1, FIG. 2, FIG. 3, or FIG. 5. For example, in an aspect there is provided a kit of parts for a thermal desorption wand, comprising: a wand body; and a swab support comprising a laminar strip configured to be coupled to the wand body so a portion of the swab support is separated from the wand body by a spacing. The swab support may comprise a heater. The kit may comprise a plurality of swab supports.

Further examples of the disclosure are defined in the appended claims.

The invention claimed is:

1. A thermal desorption apparatus, configured to detect a substance of interest in a sample, the apparatus comprising:
   a wand comprising an elongated wand body having a lateral surface and a distal tip and a swab support configured to support a swab,
   wherein the swab support is positioned over the distal tip and coupled to the wand body lateral surface and,
   wherein the swab support is configured to flex with respect to the wand body between a sample collection position and a heating position, while remaining attached to the wand body,
   wherein the swab support is deflected against the wand body in the sample collection position so that the wand body furnishes additional mechanical support to the swab for swabbing to collect a sample, and
   wherein the swab support is biased to flex away from the wand body to provide a spacing between the swab support and the distal tip of the wand body to thermally insulate the swab from the wand body while the swab is heated for thermal desorption of the sample from the swab; and
   a detector comprising an analyser arranged to detect a substance of interest;
   wherein the wand is configured to couple to the detector such that thermal desorption of the sample from the swab provides a part of the sample to the analyser.

2. The thermal desorption apparatus of claim 1, wherein the swab support is resilient.

3. The thermal desorption apparatus of claim 1, wherein the swab support comprises a heater for heating the collected sample.

4. The thermal desorption apparatus of claim 3, wherein the wand comprises an electrical coupling for coupling electrical power to the heater, wherein the coupling is arranged to electrically couple with the detector when the wand is coupled to the detector and, further comprising an electrical contact configured to engage the electrical coupling, the electrical contact being disposed on an internal portion of a housing for the detector that forms a port to receive at least a portion of the wand.

5. The thermal desorption apparatus of claim 1, wherein the swab support is disposed substantially at an end of the wand body, the wand further comprising:
   a sleeve coupled to the wand body, the sleeve configured to secure the swab to the swab support.

6. The apparatus of claim 1, wherein the swab support is resilient.

* * * * *